(12) United States Patent
Jayaraman et al.

(10) Patent No.: US 11,311,198 B2
(45) Date of Patent: *Apr. 26, 2022

(54) SYSTEM AND METHOD FOR DETERMINING PSYCHOLOGICAL STRESS OF A PERSON

(71) Applicant: Tata Consultancy Services Limited, Mumbai (IN)

(72) Inventors: Srinivasan Jayaraman, Bangalore (IN); Balamuralidhar Purushothaman, Bangalore (IN)

(73) Assignee: Tata Consultancy Services Limited, Mumbai (IN)

( * ) Notice: Subject to any disclaimer, the term of this patent is extended or adjusted under 35 U.S.C. 154(b) by 775 days.

This patent is subject to a terminal disclaimer.

(21) Appl. No.: 15/069,632

(22) Filed: Mar. 14, 2016

(65) Prior Publication Data

US 2016/0283856 A1   Sep. 29, 2016

(30) Foreign Application Priority Data

Mar. 25, 2015 (IN) ..................... IN1003/MUM/2015

(51) Int. Cl.
*A61B 5/0205* (2006.01)
*G16H 50/30* (2018.01)
(Continued)

(52) U.S. Cl.
CPC ............ *A61B 5/0205* (2013.01); *A61B 5/024* (2013.01); *A61B 5/165* (2013.01); *A61B 5/7264* (2013.01);
(Continued)

(58) Field of Classification Search
CPC ........ G06N 7/005; G06N 5/045; G06N 20/00; G16H 50/30; A61B 5/024; A61B 5/165;
(Continued)

(56) References Cited

U.S. PATENT DOCUMENTS 5,941,837 A * 8/1999 Amano .................. A61B 5/024
  600/595
6,126,595 A * 10/2000 Amano ..................... A61B 5/18
  600/300

(Continued)

FOREIGN PATENT DOCUMENTS

CN   204229589   3/2015
EP   12942776    3/2003
(Continued)

OTHER PUBLICATIONS

Healey et al., "Quantifying Driver Stress: Developing a System for Collecting and Processing Bio-Metric Signals in Natural Situations" MIT Media Laboratory Perceptual Computing Section Technical Report No. 483, Proceedings of the Rocky Mountain Bio-Engineering Symposium, Apr. 16-18, 1999. (Year: 1999).*

(Continued)

*Primary Examiner* — Luis A Sitiriche
*Assistant Examiner* — Chase P. Hinckley
(74) *Attorney, Agent, or Firm* — Finnegan, Henderson, Farabow, Garrett & Dunner, LLP (57) ABSTRACT

A system and method for determining stress level of a person in real-time have been disclosed. In one aspect, the system captures physiological data associated to the person. In one embodiment, the physiological data may be captured by using a plurality of sensors attached at wrist or ankle or neck or waist or hip of the person, for a predetermined time interval. The plurality of sensors may include a wrist watch or a wristband or a textile material. The system further pre-processes the physiological data in order to extract one or more physiological parameters. In one aspect, the pre-processing may include performing an analysis on the physiological data. The system further determines the stress level of the person upon performing the statistical analysis on the one or more physiological parameters. According to (Continued)

another embodiment, a method for real time determination of stress level of the person has also been provided.

13 Claims, 3 Drawing Sheets

(51) Int. Cl.
    *A61B 5/00*           (2006.01)
    *G16Z 99/00*         (2019.01)
    *A61B 5/024*        (2006.01)
    *A61B 5/16*          (2006.01)
    *G06N 5/04*         (2006.01)
    *A61B 5/18*          (2006.01)
    *G06N 7/00*         (2006.01)

(52) U.S. Cl.
    CPC ........... *A61B 5/7275* (2013.01); *G06N 5/045* (2013.01); *G16H 50/30* (2018.01); *G16Z 99/00* (2019.02); *A61B 5/18* (2013.01); *A61B 5/6801* (2013.01); *G06N 7/005* (2013.01)

(58) Field of Classification Search
    CPC ......... A61B 5/18; A61B 5/6801; A61B 5/742; A61B 2560/0252; A61B 5/00; A61B 5/0205; G06F 19/00; G06F 19/3431
    USPC .......................................................... 706/52
    See application file for complete search history.

(56) References Cited

U.S. PATENT DOCUMENTS

| | | | | |
|---|---|---|---|---|
| 8,100,835 B2* | 1/2012 | Baruch | ............... | A61B 5/02125 600/485 |
| 8,317,716 B2* | 11/2012 | Kim | ....................... | A61B 5/024 600/500 |
| 8,457,706 B2* | 6/2013 | Baker, Jr. | ........... | A61B 5/14551 600/323 |
| 8,552,871 B2* | 10/2013 | Park | ..................... | A61B 5/0002 340/540 |
| 8,684,922 B2* | 4/2014 | Tran | ..................... | A61B 5/6816 600/300 |
| 9,171,201 B2* | 10/2015 | Lake, II | ................. | G16H 20/30 |
| 9,183,433 B2* | 11/2015 | Amano | ............. | G06K 9/00885 |
| 9,314,181 B2* | 4/2016 | Brockway | ............. | A61B 5/046 |
| 9,408,542 B1* | 8/2016 | Kinast | ............. | A61B 5/02125 |
| 9,481,326 B2* | 11/2016 | Chatterjee | .......... | B60H 1/00657 |
| 9,532,747 B2* | 1/2017 | LaBelle | .................... | A61B 5/16 |
| 9,770,185 B2* | 9/2017 | Wheeler | ................. | A61B 5/681 |
| 9,801,553 B2* | 10/2017 | Chadderdon, III | .. | A61B 5/7264 |
| 9,820,658 B2* | 11/2017 | Tran | ..................... | A61B 5/1112 |
| 9,848,825 B2* | 12/2017 | Morris | ................. | A61B 5/6824 |
| 10,194,808 B1* | 2/2019 | Thompson | .......... | A61B 5/02028 |
| 10,213,153 B2* | 2/2019 | Atallah | .............. | A61B 5/4824 |
| 10,258,288 B2* | 4/2019 | Penders | ............... | A61B 5/7221 |
| 10,292,660 B2* | 5/2019 | Logier | ................. | A61B 5/7221 |
| 10,383,562 B2* | 8/2019 | Chan | .................. | A61B 5/02405 |
| 10,488,936 B2* | 11/2019 | Baranski | ............. | A61B 5/11 |
| 10,667,711 B1* | 6/2020 | Felix | ...................... | A61B 5/746 |
| 10,694,960 B2* | 6/2020 | Saponas | ............. | A61B 5/0059 |
| 10,824,954 B1* | 11/2020 | Tilton | ................... | G06F 3/0304 |
| 11,056,238 B1* | 7/2021 | Nakajima | ............. | G16H 40/67 |
| 11,157,436 B2* | 10/2021 | Mistry | ................... | H04W 12/06 |
| 11,166,675 B2* | 11/2021 | Baek | ...................... | A61B 5/721 |
| 2003/0149344 A1* | 8/2003 | Nizan | ..................... | G06F 3/011 600/300 |
| 2005/0096557 A1* | 5/2005 | Vosburgh | ........... | A61B 5/02125 600/509 |
| 2006/0287605 A1* | 12/2006 | Lin | .................... | A61B 5/04017 600/521 |
| 2007/0219455 A1* | 9/2007 | Wong | ................. | A61B 5/04014 600/515 |
| 2007/0265533 A1* | 11/2007 | Tran | ..................... | A61B 5/021 600/481 |
| 2008/0146892 A1* | 6/2008 | LeBoeuf | ................ | G16H 50/30 600/300 |
| 2012/0101690 A1* | 4/2012 | Srinivasan | ........... | A61B 5/0408 701/45 |
| 2012/0130196 A1* | 5/2012 | Jain | ....................... | A61B 5/0022 600/300 |
| 2012/0136226 A1* | 5/2012 | Wilke | ................. | A61B 5/02405 600/324 |
| 2012/0289791 A1* | 11/2012 | Jain | ..................... | A61B 5/4848 600/301 |
| 2012/0289793 A1* | 11/2012 | Jain | ....................... | A61B 5/165 600/301 |
| 2012/0290215 A1* | 11/2012 | Adler | ..................... | G16H 50/30 702/19 |
| 2013/0023776 A1* | 1/2013 | Olde | .................... | A61M 1/3656 600/487 |
| 2013/0096446 A1* | 4/2013 | Michael | ................ | A61B 5/0464 600/510 |
| 2013/0171599 A1* | 7/2013 | Bleich | ................. | A61B 5/0456 434/247 |
| 2013/0267796 A1* | 10/2013 | Enric Monte Moreno | ................. | A61B 5/021 600/301 |
| 2013/0281815 A1* | 10/2013 | Varadan | ............. | A61B 5/04085 600/388 |
| 2013/0338460 A1* | 12/2013 | He | ....................... | A61B 5/1455 600/324 |
| 2014/0046144 A1* | 2/2014 | Jayaraman | ............. | A61B 5/165 600/301 |
| 2014/0051941 A1* | 2/2014 | Messerschmidt | .. | A61B 5/02416 600/301 |
| 2014/0094675 A1* | 4/2014 | Luna | .................... | A61B 5/0245 600/386 |
| 2014/0121543 A1* | 5/2014 | Chan | .................... | A61B 5/0468 600/483 |
| 2014/0187941 A1* | 7/2014 | Shusterman | ........ | A61B 5/02116 600/438 |
| 2014/0206977 A1* | 7/2014 | Bahney | ................ | A61B 5/6833 600/391 |
| 2014/0221849 A1* | 8/2014 | Farringdon | ............ | A61B 5/721 600/483 |
| 2014/0249424 A1* | 9/2014 | Fan | ...................... | A61B 5/0255 600/473 |
| 2014/0275854 A1* | 9/2014 | Venkatraman | ......... | A61B 5/318 600/301 |
| 2015/0031964 A1* | 1/2015 | Bly | ........................ | A61B 5/681 600/301 |
| 2015/0057506 A1* | 2/2015 | Luna | ..................... | A61B 5/021 600/301 |
| 2015/0099987 A1* | 4/2015 | Bhatkar | ................ | G16H 30/40 600/479 |
| 2015/0112606 A1* | 4/2015 | He | ..................... | A61B 5/14542 702/19 |
| 2015/0120205 A1* | 4/2015 | Jeon | ........................ | A61B 5/015 702/19 |
| 2015/0134268 A1* | 5/2015 | Yuen | .................. | A61B 5/02007 702/19 |
| 2015/0164349 A1* | 6/2015 | Gopalakrishnan | ..... | A61B 5/746 600/508 |
| 2015/0173631 A1* | 6/2015 | Richards | ............... | A61B 5/7282 600/479 |
| 2015/0220486 A1* | 8/2015 | Karakonstantis | ..... | G06F 17/148 708/205 |
| 2015/0238140 A1* | 8/2015 | LaBelle | ................. | A61B 5/165 600/508 |
| 2015/0254414 A1* | 9/2015 | Patel | ..................... | A61B 5/6898 600/301 |
| 2015/0265161 A1* | 9/2015 | Hernandez | ........... | A61B 5/0456 600/476 |
| 2015/0282768 A1* | 10/2015 | Luna | .................. | A61B 5/02444 600/301 |
| 2015/0305675 A1* | 10/2015 | Miller | ................. | A61B 5/6823 600/301 |
| 2015/0366456 A1* | 12/2015 | Takamori | ............ | A61B 5/6898 600/480 |

(56) References Cited

U.S. PATENT DOCUMENTS

| | | | | |
|---|---|---|---|---|
| 2015/0366469 | A1* | 12/2015 | Harris | A61B 5/0205 600/301 |
| 2016/0066812 | A1* | 3/2016 | Cheng | A61B 5/0533 600/390 |
| 2016/0070393 | A1* | 3/2016 | Sharma | A61B 5/7264 345/174 |
| 2016/0120433 | A1* | 5/2016 | Hughes | G16H 80/00 600/483 |
| 2016/0157779 | A1* | 6/2016 | Baxi | A61B 5/6831 600/301 |
| 2016/0196758 | A1* | 7/2016 | Causevic | G09B 5/00 434/236 |
| 2016/0206244 | A1* | 7/2016 | Rogers | A61B 5/7246 |
| 2016/0220122 | A1* | 8/2016 | Luna | A61B 5/1102 |
| 2016/0256058 | A1* | 9/2016 | Pham | A61B 5/0205 |
| 2016/0266606 | A1* | 9/2016 | Ricci | G06F 1/163 |
| 2016/0302735 | A1* | 10/2016 | Noguchi | A61B 5/7246 |
| 2016/0338602 | A1* | 11/2016 | Oksala | A61B 5/02125 |
| 2016/0354027 | A1* | 12/2016 | Benson | A61B 5/0533 |
| 2017/0065191 | A1* | 3/2017 | Jayaraman | A61B 5/02133 |
| 2017/0238812 | A1* | 8/2017 | Atlas | A61N 1/0456 |
| 2017/0340219 | A1* | 11/2017 | Sullivan | A61B 5/681 |
| 2017/0360351 | A1* | 12/2017 | Unni | A61B 5/0205 |
| 2018/0020977 | A1* | 1/2018 | Li | A61B 5/282 600/384 |
| 2019/0083045 | A1* | 3/2019 | Borkholder | A61B 5/02007 |
| 2021/0386964 | A1* | 12/2021 | Youngblood | A47C 21/046 |

FOREIGN PATENT DOCUMENTS

| | | | | |
|---|---|---|---|---|
| EP | 3072440 A1 | * | 9/2016 | G16H 40/63 |
| KR | 20130093925 | * | 8/2013 | |
| WO | WO-199747236 A1 | * | 12/1997 | A61B 5/00 |
| WO | WO 0074551 | | 12/2000 | |
| WO | WO-2010077997 A2 | * | 7/2010 | A61B 5/0205 |

OTHER PUBLICATIONS

Rangaprakash et al., "Study of Wrist Pulse Signals Using a Bi-Modal Gaussian Model" Sep. 24-27, 2014 Indian Institute of Science, 2014 IEEE International Conference on Advances in Computing, Communications and Informatics, pp. 2422-2425 (Year: 2014).*

Hsu et al., "Skin-Coupled Personal Wearable Ambulatory Pulse Wave Velocity Monitoring System Using Microelectromechanical Sensors" Oct. 2014, IEEE Sensors Journal, vol. 14, No. 10, pp. 3490-3497. (Year: 2014).*

Liu et al., "Follow Your Heart: Heart Rate Controlled Music Recommendation for Low Stress Air Travel" Oct. 8, 2014, pp. 1-26. (Year: 2014).*

Chen et al., "Continuous and Noninvasive Blood Pressure Measurement: A Novel Modeling Methodology of the Relationship Between Blood Pressure and Pulse Wave Velocity" Nov. 2009, Annals of Biomedical Engineering, vol. 37, No. 11, pp. 2222-2233. (Year: 2009).*

Hey et al., "Continuous noninvasive Pulse Transit Time Measurement for Psycho-physiological Stress Monitoring" 2009, IEEE, International Conference on eHealth, Telemedicine, and Social Medicine, pp. 113-116. (Year: 2009).*

Al Osman, Hussein, "Ubiquitous Biofeedback Multimedia Systems" 2014, Doctoral Dissertation, University of Ottawa, pp. i-131. (Year: 2014).*

Naima, Reza, "Pervasive Health Monitoring" Fall 2012, Doctoral Dissertation, University of California Berkeley, pp. i-147. (Year: 2012).*

Tarvainen et al., "Kubios HRV: Heart rate variability analysis software" 2014, Computer Methods and Programs in Biomedicine 113, pp. 210-220. (Year: 2014).*

Liu, Qing, "Effects of Autonomic Nervous System on the Pulse Transit Time-based Blood Pressure Estimation" May 2013, Doctoral Dissertation, Chinese University of Hong Kong (Year: 2013).*

Zheng et al., "Unobtrusive Sensing and Wearable Devices for Health Informatics" 2014, IEEE Transactions on Biomedical Engineering, vol. 61, No. 5, pp. 1538-1554. (Year: 2014).*

Di Rienzo et al., "24h Seismocardiogram Monitoring in Ambulant Subjects" 2012, 34th Annual International Conference of the IEEE EMBS, pp. 5050-5053. (Year: 2012).*

McDuff et al., "Remote Measurement of Cognitive Stress via Heart Rate Variability" 2014, IEEE, pp. 2957-2960. (Year: 2014).*

Karthikeyan et al., "Detection of Human Stress Using Short-term ECG and HRV signals" 2013, Journal of Mechanics in Medicine and Biology, vol. 13, No. 2, pp. 1-29. (Year: 2013).*

Andreoli et al., "SPINE-HRV: A BSN-Based Toolkit for Heart Rate Variability Analysis in the Time-Domain" 2010, pp. 369-389. (Year: 2010).*

Muaremi et al., "Towards Measuring Stress with Smartphones and Wearable Devices During Workday and Sleep" May 8, 2013, pp. 172-183. (Year: 2013).*

Merino et al., "Stress and heart rate: significant parameters and their variations" 2014, pp. 3509-3517. (Year: 2014).*

Poh et al., "A Wearable Sensor for Unobtrusive, Long-Term Assessment of Electrodermal Activity" May 2010, IEEE, pp. 1243-1252. (Year: 2010).*

Orsila et al., "Perceived Mental Stress and Reactions in Heart Rate Variability—A Pilot Study Among Employees of an Electronics Company" Jan. 8, 2015, pp. 275-283. (Year: 2015).*

Gjoreski et al., "Towards Unobtrusive Stress Detection" 2015. (Year: 2015).*

Yoon et al., "On-chip Flexible Multi-layer Sensors for Human Stress Monitoring" 2014, IEEE, pp. 1-4. (Year: 2014).*

Vanitha et Suresh, "Hierarchical SVM to Detect Mental Stress in Human Beings Using Heart Rate Variability" 2014, IEEE, pp. 1-5. (Year: 2014).*

Xu et al., "Cluster-Based Analysis for Personalized Stress Evaluation using Physiological Signals" Mar. 11, 2014, IEEE, pp. 275-281. (Year: 2014).*

Goodwin, Tom, "Expectations for the Apple iWatch, Your Interface with the Digital World" http://www.linkedin.com/today/post/article/20140624134124-6433797-introducing-the-apple-iwatch-your-interface-with-the-digital-world, Jun. 24, 2014, pp. 8. (Year: 2014).*

Rainmaker, DC, "A look at AmpStrip—the really cool heart rate sticker & activity tracker" https://www.dcrainmaker.com/2015/01/ampstripthe-sticker-activity.html, Jan. 6, 2015, pp. 52. (Year: 2015).*

Rainmaker, "Hands on with Samsung's new waterproof S5, activity tracker and Gear watches—with built-in heart rate sensor", http://www.dcrainmaker.com/2014/02/waterproof-activity-watcheswith.html, Feb. 24, 2014, pp. 79. (Year: 2014).*

Hughes et al., U.S. Appl. No. 62/073,910 "Wearable Monitor" Oct. 31, 2014. (Year: 2014).*

Chakrabarty et al., "Correcting Hypothalamic-Pituitary-Adrenal Axis Dysfunction Using Observer-based Explicit Nonlinear Model Predictive Control" 2014, pp. 3426-3429. (Year: 2014).*

Sullivan et al., "Electrical Coupling of Pulse Transit Time (PTT) Measurement System to Heart for Blood Pressure Measurement" Sep. 8, 2014, U.S. Appl. No. 62/047,486. (Year: 2014).*

Tilton et al., "Methods and Apparatus for Learning Sensor Data Patterns of Physical-Training Activities" Jun. 25, 2014, U.S. Appl. No. 62/017,227. (Year: 2014).*

Bogomolov et al., "Daily Stress Recognition from Mobile Phone Data, Weather Conditions, and Individual Traits" Oct. 21, 2014. (Year: 2014).*

Peter et al., "A review of methods for non-invasive and continuous blood pressure monitoring: Pulse transit time is promising?" Aug. 28, 2014, pp. 271-282. (Year: 2014).*

Healey, J. et al., "Quantifying Driver Stress: Developing a System for Collecting and Processing Bio-Metric Signals in Natural Situations", M.I.T. Media Laboratory Perceptual Computing Section Technical Report No. 483, pp. 1-6, (1999).

* cited by examiner

SYSTEM AND METHOD FOR DETERMINING PSYCHOLOGICAL STRESS OF A PERSON

CROSS-REFERENCE TO RELATED APPLICATIONS AND PRIORITY

The present application claims priority from Indian provisional specification no. 1003/MUM/2015 filed on 25, Mar. 2015, the complete disclosure of which, in its entirety is herein incorporated by references.

TECHNICAL FIELD

The present subject matter described herein, in general, relates to a system and a method for determining a stress level of a person in real-time, and more particularly to the system and the method for determining the stress level based on physiological data associated to the person.

BACKGROUND

Stress level of a person is one of the biomarker or indicators of the health of the person. On the other hand, stress in the working environment can lead to poor health and even injury. Common complaints due to stress include loss of concentration; mood and sleep disturbances, upset stomach, cardiac disorder and headache. Measurement of stress may provide inference or act as an indicator about the physiological and psychological health of the person. Therefore, continuous monitoring of an individual stress level is essential for managing personal health and wellness. In order to determine the stress level, various methods have been used by the caregivers.

In order to characterize the stress level of the person, currently the following techniques are being performed: a) questionnaires, b) Electroencephalogram (EEG), c) face expression, d) Photoplethysmogram (PPG) and e) Electrocardiogram (ECG). One of the methods involves monitoring physiological signals, such as electrocardiogram (ECG) signals, of the person to ascertain the stress level for managing personal stress assessment. Current methods of monitoring the physiological signals include measuring the physiological signals over duration of time, either by inducing stress among participants by making them undergo a stress test or by performing a relaxation exercise. On the other hand, the traditional approaches for detecting the stress level have used more electrodes or location of electrode and long duration of event base recording. For example, the ECG or the EEG based approaches may require minimum of two electrodes at two different locations. As an addendum, such traditional approaches also use threshold technique for detecting the stress level of the person. In another technique, stress can be measured by determining the level of the hormone cortisol in the blood; which is an invasive technique of measurement. Cortisol is a corticosteroid hormone that is involved in the response to stress.

Yet another technique uses monitoring stress related pattern of muscle activity. However, these devices require skin-contacted electrodes in order to gather stress status data, so that the actual application of these devices is very annoying to the user. Moreover, the known devices are bound to influence the state of relaxation of the user in a negative way. A lot of traditional techniques have also been explored for the determination of stress level. One of the traditional techniques involves use of Hrallasika method. Hrallasika means palpation of heart from Sanskrit. In traditional medical approach, the pulse palpations were followed for disease diagnosis tool. This technique has not been explored for the stress determination or similar diagnostic purpose.

However, none of the traditional approaches had addressed detection of the stress level in real-time and in addendum single sensing technique. In addition, no system in existence manages the psychological and cardiac system of the person.

SUMMARY

Embodiments of the present disclosure present technological improvements as solutions to one or more of the above-mentioned technical problems recognized by the inventors in conventional systems.

In one implementation, a system and a processor implemented method for determining a stress level of a person in real-time is disclosed. The present invention may be used to capture physiological data associated to the person. In one embodiment, the physiological data may be captured by using a single or an array of sensors attached to wrist or ankle or neck or waist of the person. In one aspect, the array of sensor could be 2 or more sensing element embodied as a sensor. In one aspect, in order to measure the arterial pulse palpation rate, a sensor may be attached to the wrist of the person by using the wristwatch or the wristband or the textile as a cuff. The system further includes a transmitter, a storage device and a processor. The transmitter transmits the stream of pulse palpation signal to the processor. The processor further includes a preprocessing module and a decision support system module. The preprocessing module preprocesses the stream of arterial pulse palpation signal to extract a plurality of physiological parameters. The decision support module performs a statistical modal analysis of the plurality of physiological parameters and determines the stress level of the person based on the statistical modal analysis.

In another embodiment, the present invention may capture the physiological data by using an integrated smart phone sensor. It may be understood that the present invention may require minimum of 1 minute of the arterial pulse palpation rate. In one scenario, the present invention may capture the physiological data and transmit the physiological data to a smart phone or an external device having a decision support system (DSS) module installed on the smart phone or the external device. Once the physiological data is transmitted, the smart phone may receive the physiological data and perform analysis on the physiological data to determine the stress level. In one aspect, the DSS application may upload the physiological data to a central server where further cardiac clinical analysis may be performed.

In one embodiment, the DSS application may be capable of receiving status information pertaining to the person such as standing, sitting, running and so on from the integrated smart phone sensor. In another scenario, the present invention may provide the stress level of the person based on the integrated smart phone sensor.

In another embodiment, a processor implemented method has also been provided for measuring the real time stress of the person. Initially, at least one stream of arterial pulse palpation signal is sensed for a predefined time period using a plurality of sensors. The sensed stream of arterial pulse palpation signal is transmitted to the processor. The stream of arterial pulse palpation signal is then preprocessed to extract a plurality of physiological parameters using the preprocessing module. Finally a statistical modal analysis of the plurality of physiological parameters is performed by a decision support module present in the processor to determine the stress level of the person.

In another embodiment, a non-transitory computer-readable medium having embodied thereon a computer program for determining a stress level of a person in real time has also been provided. Initially, at least one stream of arterial pulse palpation signal is sensed for a predefined time period using a plurality of sensors. The sensed stream of arterial pulse palpation signal is transmitted to the processor. The stream of arterial pulse palpation signal is them preprocessed to extract a plurality of physiological parameters using the preprocessing module. Finally a statistical modal analysis of the plurality of physiological parameters is performed by a decision support module present in the processor to determine the stress level of the person.

It is to be understood that both the foregoing general description and the following detailed description are exemplary and explanatory only and are not restrictive of the invention, as claimed.

BRIEF DESCRIPTION OF THE DRAWINGS

The foregoing detailed description of embodiments is better understood when read in conjunction with the appended drawings. For the purpose of illustrating the disclosure, there are shown in the present document example constructions of the disclosure. However, the disclosure is not limited to the specific methods and apparatus disclosed in the document and the drawings.

The detailed description is described with reference to the accompanying figures. In the figures, the left-most digit(s) of a reference number identifies the figure in which the reference number first appears. The same numbers are used throughout the drawings to refer like features and components.

The Figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION OF THE INVENTION

Some embodiments of this invention, illustrating all its features, will now be discussed in detail.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any systems and methods similar or equivalent to those described herein can be used in the practice or testing of embodiments of the present invention, the preferred, systems and methods are now described. In the following description for the purpose of explanation and understanding reference has been made to numerous embodiments for which the intent is not to limit the scope of the invention.

One or more components of the invention are described as module for the understanding of the specification. For example, a module may include self-contained component in a hardware circuit comprising of logical gate, semiconductor device, integrated circuits or any other discrete component. The module may also be a part of any software program executed by any hardware entity for example processor. The implementation of module as a software program may include a set of logical instructions to be executed by a processor or any other hardware entity.

The disclosed embodiments are merely exemplary of the invention, which may be embodied in various forms.

Method steps of the invention may be performed by one or more computer processors executing a program tangibly embodied on a computer-readable medium to perform functions of the invention by operating on input and generating output. Suitable processors include, by way of example, both general and special purpose microprocessors. Generally, the processor receives (reads) instructions and data from a memory (such as a read-only memory and/or a random access memory) and writes (stores) instructions and data to the memory. Storage devices suitable for tangibly embodying computer program instructions and data include, for example, all forms of non-volatile memory, such as semiconductor memory devices, including EPROM, EEPROM, and flash memory devices; magnetic disks such as internal hard disks and removable disks, magneto-optical disks, and CD-ROMs. Any of the foregoing may be supplemented by, or incorporated in, specially-designed ASICs (application-specific integrated circuits) or FPGAs (Field-Programmable Gate Arrays). A computer can generally also receive (read) programs and data from, and write (store) programs and data to, a non-transitory computer-readable storage medium such as an internal disk (not shown) or a removable disk.

In one implementation, a system and a method for determining a stress level of a person in real-time is disclosed. The present invention may be used to capture physiological data associated to the person. In one embodiment, the physiological data may be captured by using a plurality of sensors attached to wrist or ankle or neck or waist of the person. In one aspect, in order to measure the arterial pulse palpation rate, a sensor may be attached to the wrist of the person by using the wrist watch or the wristband or the textile as a cuff. The system further includes a transmitter, a storage device and a processor. The transmitter transmits the stream of pulse palpation signal to the processor. The processor further includes a preprocessing module and a decision support system module. The preprocessing module preprocesses the stream of arterial pulse palpation signal to extract a plurality of physiological parameters. The decision support module performs a statistical modal analysis of the plurality of physiological parameters and determines the stress level of the person based on the statistical modal analysis.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Figure 1:
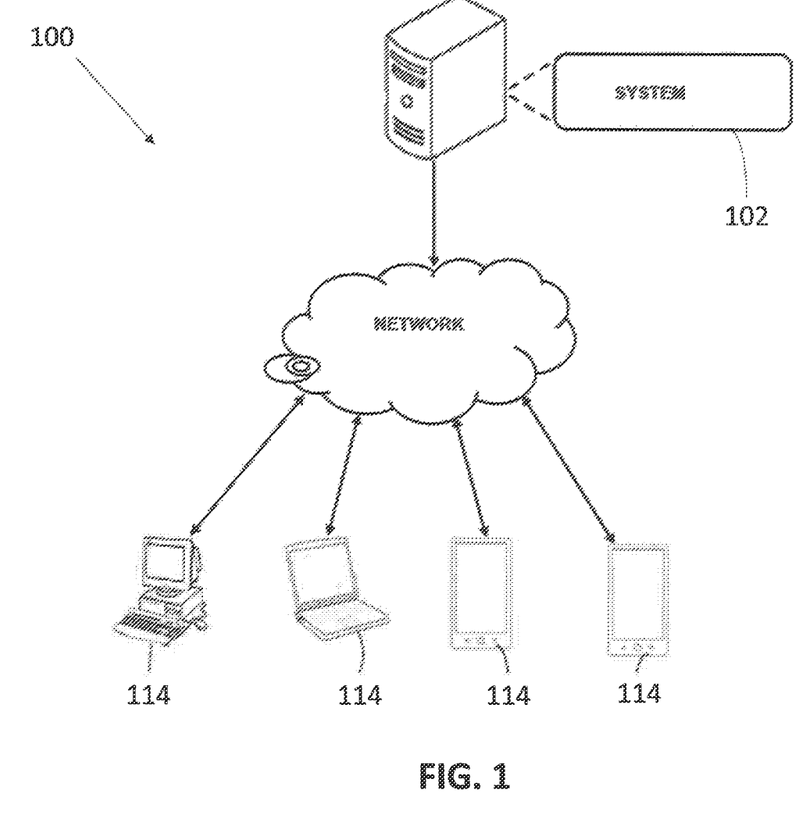
FIG. 1 illustrates a network implementation of a system for determining a stress level of a person in real-time, in accordance with an embodiment of the present disclosure.

According to an embodiment of the invention, a network implementation 100 of a system 102 for determining a stress level of a person in real-time, is shown in FIG. 1. In one aspect, the system 102 captures a plurality of physiological data associated to the person. In one embodiment, the plurality of physiological data may be captured by using a plurality of sensors 104. In one aspect the plurality of sensors 104 are the non-invasive plurality of sensors 104. The plurality of sensors 104 are attached to wrist or ankle or neck or waist or hip of the person. For example, a wristwatch or a wristband or a textile material such as cuff to measure the arterial pulse palpation rate or biological parameter. In one aspect, the arterial pulse palpation rate captured, from the plurality of sensors 104, for a predetermined ultra-short or short duration. The system 102 further pre-processes the physiological data in order to extract a plurality of physiological parameters. In one aspect, the pre-processing may include performing an analysis on the physiological data. The system 102 further determines the stress level of the person in the real-time based upon performing the statistical modal analysis of the plurality of physiological parameters.

Although the present subject matter is explained considering that the server (not shown) is implemented as a computing system, it may be understood that the server may also be implemented as a variety of computing systems, such as a laptop computer, a desktop computer, a notebook, a workstation, a mainframe computer, a server, a network server, a tablet, a mobile phone, and the like. In one implementation, the server may be implemented in a cloud-based environment. According to an embodiment, the system 102 may be implemented with the vehicle. Further, the server may track the activities of the system 102, and the system 102 is communicatively coupled to the server 102 through the network 100.

In one implementation, the network 100 may be a wireless network, a wired network or a combination thereof. The network 100 can be implemented as one of the different types of networks, such as intranet, local area network (LAN), wide area network (WAN), the internet, and the like. The network 100 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further the network 100 may include a variety of network devices, including routers, bridges, servers, computing devices, storage devices, and the like.

Figure 2:
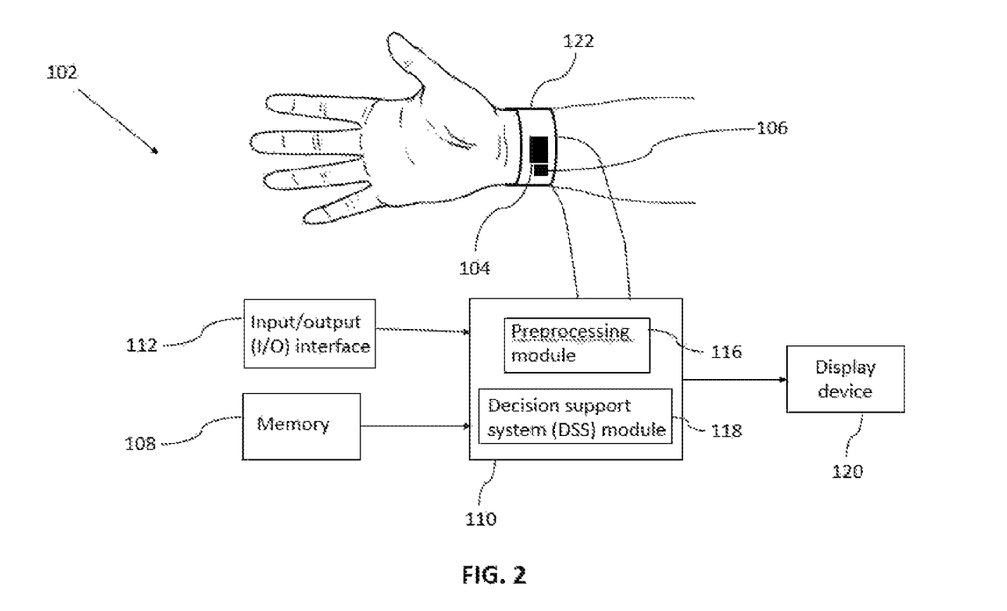
FIG. 2 illustrates the system for determining the stress level of the person, in accordance with an embodiment of the present disclosure.

According to an embodiment of the invention, the system 102 for determining the stress of the person is shown in FIG. 2. In one embodiment, the system 102 includes a plurality of sensors 104, a transmitter 106, a storage device 108 or a memory 108 and at least one processor 110. The system 102 also includes an input/output (I/O) interface 112. The processor 110 may be implemented as one or more microprocessors, microcomputers, microcontrollers, digital signal processors, central processing units, state machines, logic circuitries, and/or any devices that manipulate signals based on operational instructions. Among other capabilities, the processor 110 is configured to fetch and execute computer-readable instructions stored in the memory 108.

The I/O interface 112 may include a variety of software and hardware interfaces, for example, a web interface, a graphical user interface, and the like. The I/O interface 112 may allow the system 102 to interact with the user directly or through a plurality of client devices 114. Further, the I/O interface 112 may enable the system 102 to communicate with other computing devices, such as web servers and external data servers (not shown). The I/O interface 112 can facilitate multiple communications within a wide variety of networks and protocol types, including wired networks, for example, LAN, cable, etc., and wireless networks, such as WLAN, cellular, or satellite. The I/O interface 112 may include one or more ports for connecting a number of devices to one another or to another server.

The memory 108 may include any computer-readable medium and computer program product known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes.

The processor 110 further includes a preprocessing module 116 and a decision support system (DSS) module 118. The modules generally include routines, programs, objects, components, data structures, etc., which perform particular tasks or implement particular abstract data types. The pre-processing module 116 and the decision support system (DSS) module 118 may include programs or coded instructions that supplement applications and functions of the system 102. The modules 116 and 118 described herein may be implemented as software modules that may be executed in the cloud-based computing environment of the system 102. In another embodiment the processor 110 may also include other modules performing various other functions of the system 102.

In one implementation, a system and a method for determining a stress level of a person in real-time is disclosed. The present invention may be used to capture physiological data associated to the person. In one embodiment, the physiological data may be captured by using the plurality of sensors 104. The plurality of sensors 104 can be attached to a primary location of the person such as wrist or ankle or neck or waist or hip to sense the arterial pulse palpation rate. For example, a wrist watch or a wristband or a textile material such as cuff to measure the arterial pulse palpation rate or biological parameter. In one example, in order to measure the arterial pulse palpation rate, an external sensor may be attached to the wrist of the person by using the wrist watch or the wristband or the textile as a cuff. Examples of the one or more external sensors may include, but not limited to, a piezo-electric sensor or a piezo-resistive sensor. It may be understood that the external sensor senses the arterial pulse palpation rate of the person and thereby captures the physiological data associated to the person.

According to an embodiment, the arterial palpation signal is captured from at least one of a temporal artery, a facial artery, a carotid artery, a brachial artery, a radial artery, a femoral artery, a popliteal artery, a popliteal tibial artery and a dorsalis pedis artery of the person.

In another embodiment, the present invention may capture the physiological data by using an integrated smart phone sensor. It may be understood that the present invention may require minimum of 1 minute of the arterial pulse palpation rate. In one scenario, the present invention may capture the physiological data (including the arterial pulse palpation rate) and transmit the physiological data to a smart phone having the decision support system (DSS) module 118 or the decision support module 118 on the smart phone or an external device. Once the physiological data is transmitted, the smart phone may receive the physiological data and perform statistical modal analysis on the physiological data in order to determine the stress level. In one aspect, upon determining the stress level, the system 100 may display or generates an audio alarm to provide the outcome of the analysis to indicate the stress level of the person. The system 102 further includes a display device 120 to display the stress level. Further, the DSS module may upload the physiological data to a central server where further cardiac clinical analysis may be performed.

In one aspect, the DSS module 118 may be capable of receiving status information pertaining to the person from the integrated smart phone sensor. The status information may include, but not limited to, standing, sitting, and running. In one aspect, the arterial pulse palpation rate may be fused with the status information of the person to improve the accuracy of the status information. In one aspect, an additional sensor located near to the primary location may facilitate to determine the Pulse Wave Velocity (PVW). In one aspect, the system 102 may detect the PWV in the same segment of artery or location with ultra-short duration signal (i.e. 1 minute of arterial pulse palpation rate). In one aspect, the determination of the PWV in addition to the existing system, may help in determining the status information of the person and thereby help in improving the accuracy of the stress level of the person.

Yet another aspect, the DSS module 118 may be capable of receiving environment temperature information from the integrated smart phone sensor or smart watch sensor. In one aspect, the arterial pulse palpation rate may be fused with the temperature information to improve the accuracy of the stress information.

Further the DSS module 118 is configured to analyze the extracted physiological parameters to determine the stress level. In an example, a pulse signal captured from the person. The pulse signal is analyzed as follows: At step 1, the raw pulse data of mV signal is acquired through surface piezo electrode (not shown) and amplified to Voltage signal X(n) at three different location of wrist. The Raw signals were pre-processed and peak-to-peak (PP) intervals PP (X) were extracted. At step 2: For example PP Interval PP(X) was interpolated and feature parameters F(x) are extracted. The features parameters F(x) extracted for all the enrolled users stored in a database. Once the probe data is determined, step 1 and step 2 may be performed. Further, the probe data may be matched with the database comprising the feature parameters F(x) by using a statistical model or classification or matching techniques. During the classification or the matching technique, one or more features listed in table may be used to determine the stress level.

Figure 3:
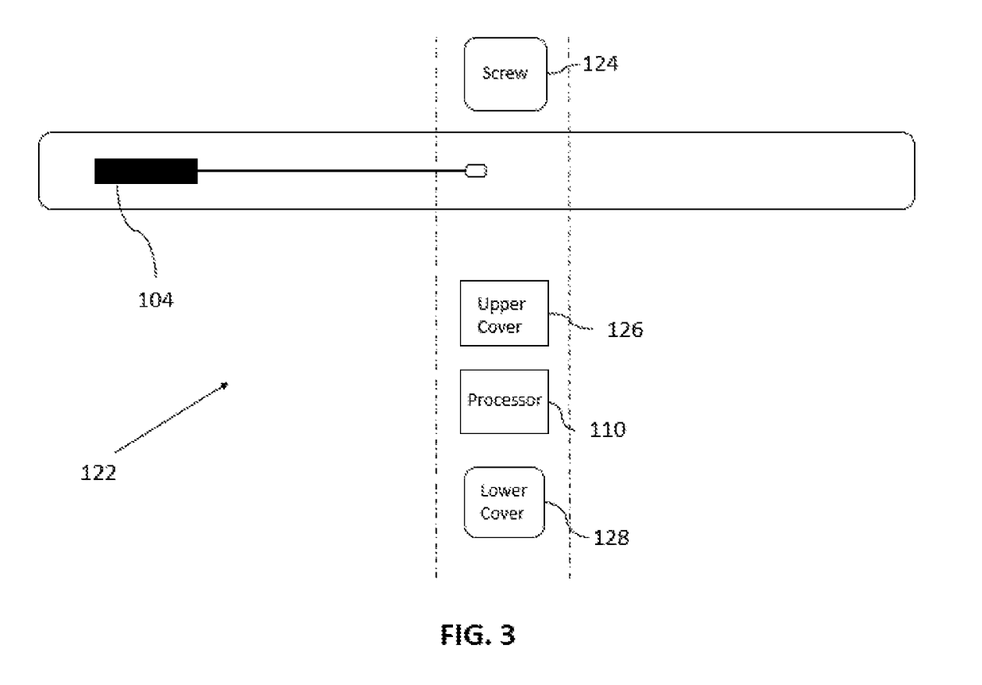
FIG. 3 illustrates a wearable sensor to monitor an arterial pulse palpation rate in the wrist, in accordance with an embodiment of the present disclosure.

FIG. 3 illustrates a wearable sensor 122 to monitor the arterial pulse palpation rate in the wrist according to an embodiment of the invention. An exploded view of the wearable sensor 122 for determining the stress of the person shown in FIG. 3. The figure shows the wearable sensor 122 including a screw 124, an upper cover 126, a lower cover 128 and the processor 110 which can be fitted between the upper cover 126 and the lower cover 128.

As shown in the FIG. 3, a standalone sensor may be attached to the wrist of the person in order to determine the stress level. In addition to monitor the arterial pulse palpation rate, the wearable sensing unit may be used to determine the Pulse Wave Velocity (PWV).

Figure 4:
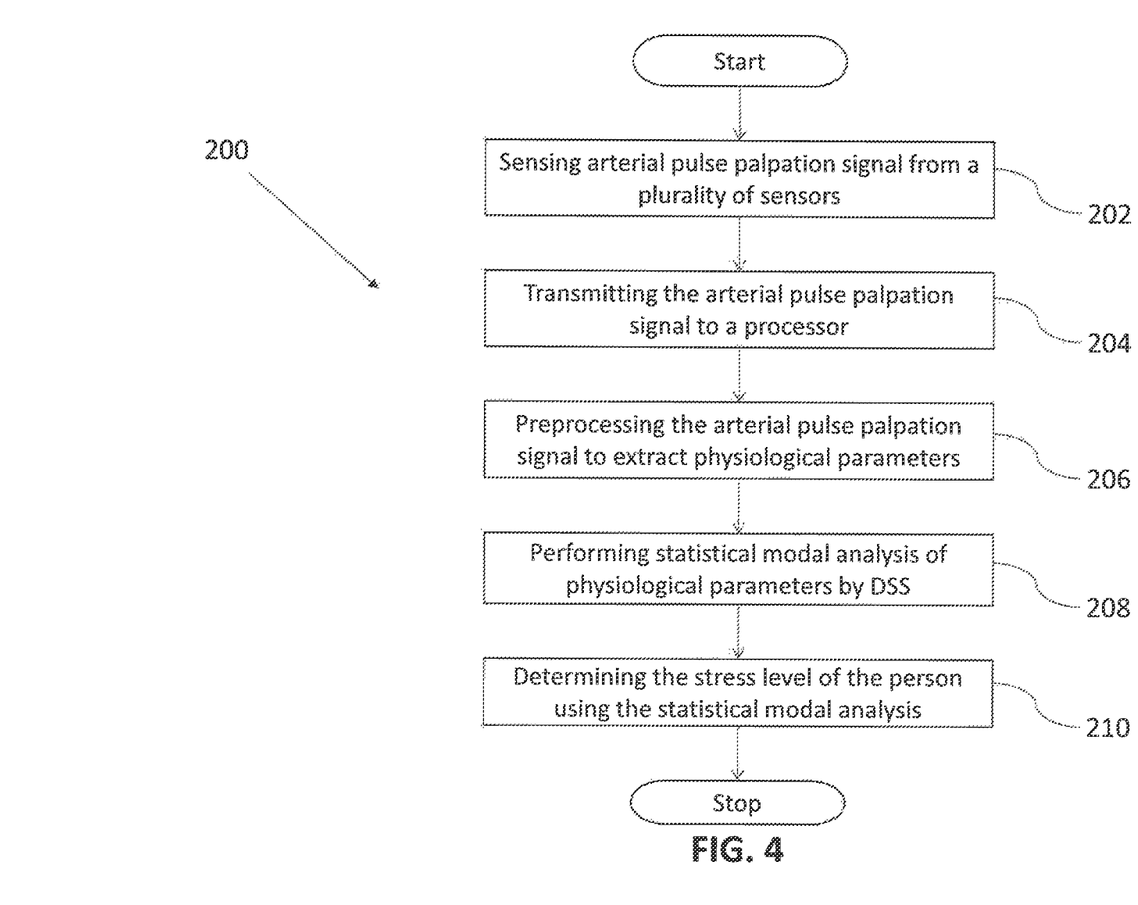
FIG. 4 illustrates the flow chart for determining the stress level, in accordance with an embodiment of the present disclosure.

FIG. 4 illustrates the flow chart 200 for determining the stress level of a person according to an embodiment of the invention. Initially at step 202, at least one stream of arterial pulse palpation signal is sensed using the plurality of sensors 104. The sensing is done only for a predefined time period, in an example, the signal is sensed for about one minute. At the next step 204, the sensed pulse palpation signal is transmitted to the processor 110 using the transmitter 106. The processor 110 further includes a plurality of modules such as the preprocessing module 116 and the decision support system (DSS) module 118. At step 206, the stream of arterial pulse palpation signal is preprocessed using the preprocessing module 116 to extract the plurality of physiological parameters. At the next step 208, the statistical modal analysis of the extracted plurality of physiological parameters is performed using the DSS module 118. The DSS module 118 can be present on the smart phone or can be present on an external device. And finally at step 210, the stress level of the person is determined using the statistical modal analysis of the plurality of physiological parameters.

According to another embodiment of the invention, the system 102 can further provide an alert to a caregiver/doctor in case the stress level moves out of a predefined conditions. It should be appreciated that the system 102 can further provides a plurality of features to reduce the stress of the person.

According to another embodiment of the invention, the system 102 is synchronized with an entertainment system in a vehicle and the pulse palpation system 102 is configured to measure the stress level of a driver driving the vehicle. In case, the stress level moves out of the predefined conditions then the system 102 can interrupt or initiate the entertainment system of the vehicle. The entertainment system can be personalized in such a way that as soon as the stress level moves out of the predefined condition then a personalized music playlist can be played based on the choice of the driver, in order to reduce the stress level of the driver. In another example, a mobile phone of the user can also be personalized. In yet another example, the mobile gaming alert can also be personalized.

Exemplary embodiments discussed above may provide certain advantages. Though not required to practice aspects of the disclosure, these advantages may include those provided by the following features.

Some embodiments enable a system and a method to continuous monitor a stress level of a person in real-time by integrating non-invasive one or more external sensors at one location like sensor attached at their wrist or ankle or neck or waist of the person.

Some embodiments enable a system and a method to facilitate the person to measure or alert the stress level without cumbersome electrode placement all over the body or group of region associated to the person.

Some embodiments enable a system and a method to assist the person to determine the stress level in short duration by capturing arterial pulse palpation rate for 1 minute duration.

Some embodiments enable a system and a method to determine the stress level in offline or real-time rather than inducing stress among the participants by making them undergo a stress test or perform a relaxation exercise.

Some embodiments enable a system and a method to determine Pulse Wave Velocity (PWV) of the system using more than one electrode system with same part or location of the person body.

Some embodiments enable a system and method to improve the determined the stress level by adding an external or inbuilt atmosphere or environmental temperature.

It should be appreciated the device and method can also be used for the estimation of other parameters of the person such as heart rate, etc. It should also be appreciated that the device can also be implemented using a wearable sensor for estimating heart palpitation based on pulse of blood vessels.

In view of the foregoing, it will be appreciated that the present invention provides a method and device for the continuous estimation of the blood pressure using palpation signal captured from the artery. Still, it should be understood that the foregoing relates only to the exemplary embodiments of the present invention, and that numerous changes may be made thereto without departing from the spirit and scope of the invention as defined by the following claims.

What is claimed is:

1. A real time method for determining a stress level of a person, the method comprising a processor implemented steps of:
    sensing at least one stream of arterial pulse signal from an arterial pulse palpation rate measured at a radial artery of the person using at least one non-invasive external sensor for one minute duration, wherein the at least one non-invasive external sensor is attached to a wrist of the person as one of a wrist watch or a wristband or a textile material as a cuff, wherein the sensor is at least one of a piezoelectric sensor or a piezoresistive sensor;
    transmitting the stream of arterial pulse signal by a transmitter to the processor;
    preprocessing the stream of arterial pulse signal to extract a plurality of physiological parameters by the processor;
    detecting a pulse wave velocity using an additional sensor for one minute duration, wherein the additional sensor is at least one of the piezoelectric sensor or the piezoresistive sensor, wherein the pulse wave velocity is further used for determining a status information of the person based on physiological data captured by an integrated smart phone sensor, wherein the pulse wave velocity is detected at three locations of the radial artery at the same wrist where the arterial pulse signal is sensed for acquiring a raw pulse data of mV signal, wherein the arterial pulse signal is fused with the status information of the person to improve accuracy of determining the stress level of a person, and wherein the status information includes standing, sitting and running;
    performing a statistical modal analysis of the plurality of physiological parameters, the pulse wave velocity and the status information fused with arterial pulse signal, by:
        acquiring the raw pulse data of mV signal;
        amplifying the raw pulse data to Voltage signal and pre-processing the raw pulse data to extract peak-to-peak intervals for each of said three locations; and
        extracting feature parameters by interpolating the extracted peak-to-peak intervals, of said three locations, with each other, wherein the extracted feature parameters are stored in a data base; and
    determining the stress level of the person using the statistical modal analysis of the plurality of physiological parameters upon determining a match between the plurality of physiological parameters and the feature parameters in the database that includes feature parameters of multiple persons.

2. The method of claim 1 further includes uploading the physiological parameters by the processor to a central server for performing a cardiac clinical analysis.

3. The method of claim 1, further comprising providing additional information for the statistical analysis using an input interface.

4. The method of claim 1 further comprising providing an alert to a caregiver if stress level moves out of a predefined condition.

5. The method of claim 1, wherein the person is driving a vehicle.

6. The method of claim 5 further comprising interruption or initiation of the vehicle music system, when the determined stress level of the person exceeds a predefined condition, wherein a personalized music is initiated to reduce the stress level of the person, wherein the personalized music is played from a personalized music playlist based on choice of the person.

7. The method of claim 1 further comprising providing ambient temperature of the environment.

8. A system for determining a stress level of a person in real time, the system comprising:
    at least one non-invasive external sensor attached to the person, the sensor configured to sense at least one stream of arterial pulse signal from an arterial pulse palpation rate measured at a radial artery of the person for one minute duration, wherein the at least one non-invasive external sensor is attached to a wrist of the person as one of a wrist watch or a wristband or a textile material as a cuff, wherein the sensor is at least one of a piezoelectric sensor or a piezoresistive sensor;
    a transmitter for transmitting the stream of arterial pulse signal;
    a storage device; and
    a processor coupled to the memory, the processor comprising,
        a preprocessing module configured for:
            preprocessing the stream of arterial pulse signal to extract a plurality of physiological parameters;
            detecting a pulse wave velocity using an additional sensor for one minute duration, wherein the additional sensor is at least one of the piezoelectric sensor or the piezoresistive sensor, wherein the pulse wave velocity is further used for determining a status information of the person based on physiological data captured by an integrated smart phone sensor, wherein the pulse wave velocity is detected at three locations of the radial artery at the same wrist where the arterial pulse signal is sensed for acquiring a raw pulse data of mV signal, wherein the arterial pulse signal is fused with the status information of the person to improve accuracy of determining the stress level of a person, and wherein the status information includes standing, sitting and running; and
        a decision support module for:
            performing a statistical modal analysis of the plurality of physiological parameters, the pulse wave velocity and the status information fused with arterial pulse signal, by:
                acquiring the raw pulse data of mV signal;

amplifying the raw pulse data to Voltage signal and pre-processing the raw pulse data to extract peak-to-peak intervals for each of said three locations; and extracting feature parameters by interpolating the extracted peak-to-peak intervals, of said three locations, with each other, wherein the extracted feature parameters are stored in a data base; and determining the stress level of the person based on the statistical modal analysis of the plurality of physiological parameters upon determining a match between the plurality of physiological parameters and the feature parameters in the database that includes feature parameters of multiple persons.

9. The system of claim 8 further includes a display device for displaying the outcome of the statistical modal analysis.

10. The system of claim 8, wherein the decision support module is inbuilt in a smart phone of the user.

11. The system of claim 8, wherein the arterial signal is captured from at least one of a temporal artery, a facial artery, a carotid artery, a brachial artery, a radial artery, a femoral artery, a popliteal artery, a popliteal tibial artery and a dorsalis pedis artery of the person.

12. The system of claim 8 further includes a user interface to provide additional information for the statistical modal analysis.

13. A non-transitory computer-readable medium having embodied thereon a computer program for determining a stress level of a person in real time, the method comprising:

sensing at least one stream of arterial pulse signal from an arterial pulse palpation rate measured at a radial artery of the person using at least one non-invasive external sensor for one minute duration, wherein the at least one non-invasive external sensor is attached to a wrist of the person as one of a wrist watch or a wristband or a textile material as a cuff, wherein the sensor is at least one of a piezoelectric sensor or a piezoresistive sensor;

transmitting the stream of arterial pulse signal by a transmitter to a processor;

preprocessing the stream of arterial pulse signal to extract a plurality of physiological parameters by the processor;

detecting a pulse wave velocity using an additional sensor for one minute duration, wherein the additional sensor is at least one of the piezoelectric sensor or the piezoresistive sensor, wherein the pulse wave velocity is further used for determining a status information of the person based on physiological data captured by an integrated smart phone sensor, wherein the pulse wave velocity is detected at three locations of the radial artery at the same wrist where the arterial pulse signal is sensed for acquiring a raw pulse data of mV signal, wherein the arterial pulse signal is fused with the status information of the person to improve accuracy of determining the stress level of a person, and wherein the status information includes standing, sitting and running;

performing a statistical modal analysis of the plurality of physiological parameters, the pulse wave velocity and the status information fused with arterial pulse signal, by:

acquiring the raw pulse data of mV signal;

amplifying the raw pulse data to Voltage signal and pre-processing the raw pulse data to extract peak-to-peak intervals for each of said three locations; and extracting feature parameters by interpolating the extracted peak-to-peak intervals, of said three locations, with each other, wherein the extracted feature parameters are stored in a data base; and determining the stress level of the person using the statistical modal analysis of the plurality of physiological parameters upon determining a match between the plurality of physiological parameters and the feature parameters in the database that includes feature parameters of multiple persons.

\* \* \* \* \*